United States Patent
Van Handel

[19]

[11] Patent Number: 6,149,427
[45] Date of Patent: *Nov. 21, 2000

[54] METHOD AND APPARATUS FOR FABRICATING AND FITTING DENTURES

[75] Inventor: William J. Van Handel, 2800 Walton Pl., El Dorado Hills, Calif. 95762

[73] Assignee: William J. Van Handel, El Dorado Hills, Calif.; living trust

[*] Notice: This patent is subject to a terminal disclaimer.

[21] Appl. No.: 09/393,076

[22] Filed: Sep. 7, 1999

Related U.S. Application Data

[63] Continuation of application No. 08/843,912, Apr. 17, 1997, Pat. No. 5,961,325.

[51] Int. Cl.⁷ ................................................. A61C 13/00
[52] U.S. Cl. ................................................. 433/37; 433/44
[58] Field of Search .................................... 433/26, 37, 44, 433/167, 214, 68; 206/63.5, 83

[56] References Cited

U.S. PATENT DOCUMENTS

| | | |
|---|---|---|
| 1,083,156 | 12/1913 | Telle . |
| 1,778,293 | 10/1930 | Galasso . |
| 1,931,804 | 10/1933 | Sanborn . |
| 2,229,780 | 1/1941 | Vaillancourt . |
| 2,412,352 | 12/1946 | Myerson . |
| 2,588,169 | 3/1952 | Shea ........................................ 433/214 |
| 2,685,133 | 8/1954 | Greene et al. . |
| 2,758,374 | 8/1956 | Fisher et al. . |
| 3,335,495 | 8/1967 | Wichner . |
| 3,460,252 | 8/1969 | Schneider et al. . |
| 3,465,440 | 9/1969 | Gareis ........................................ 433/171 |
| 3,473,225 | 10/1969 | Deuschle et al. . |
| 3,644,996 | 2/1972 | Weinkle . |
| 3,909,944 | 10/1975 | Schmidt et al. . |
| 4,146,963 | 4/1979 | Schreinemakers . |
| 4,227,877 | 10/1980 | Tureaud et al. . |
| 4,235,594 | 11/1980 | Schwartz . |
| 4,245,988 | 1/1981 | Cinotti et al. ........................... 433/68 |
| 4,247,287 | 1/1981 | Gigante . |

(List continued on next page.)

FOREIGN PATENT DOCUMENTS

| | | |
|---|---|---|
| 1079793 | 4/1960 | Germany . |
| 26 42 976 | 3/1978 | Germany . |
| 3239528 | 5/1984 | Germany . |
| 3529-764 | 5/1986 | Germany . |
| 3910393 | 4/1990 | Germany . |
| 2 196 260 | 4/1988 | United Kingdom . |
| WO 80/01240 | 6/1980 | WIPO ....................................... 433/37 |

OTHER PUBLICATIONS

Krantz, W. et al., "Combining Final Impressions and the Centric Jaw Relation Records into One Appointment by Using an Irreversible Hydrocolloid Blockout Technique", The Journal of Prosthetic Dentistry, vol. 66, PG 821–2, Dec. 1991.

*Primary Examiner*—Ralph A. Lewis
*Attorney, Agent, or Firm*—John P. O'Banion

[57] ABSTRACT

An apparatus and method for fabricating and fitting dentures that employs a Biteblock/Impression Tray and a Preset Teeth Carrying Tray. The Biteblock/Impression Tray is produced for both upper and lower dental arches with a wax biteblock attached to each, and shaped with flanges and a palate on the upper tray to accommodate the taking of impressions. The Preset Teeth Carrying Tray is produced for both upper and lower dental arches with the denture teeth mounted in their anatomical position to a plastic tray using wax that is festooned around the teeth and simulates the gum tissue. Each denture tooth is produced with a retention groove below the gum line and has the glaze removed from the roots prior to being mounted in the wax on the Preset Teeth Carrying Tray. Since the teeth are in their correct anatomical position with wax simulating the gum tissue, the teeth can be easily transferred as a unit to a stone model of the patient's dental arch for denture fabrication.

6 Claims, 8 Drawing Sheets

U.S. PATENT DOCUMENTS

| | | |
|---|---|---|
| 4,259,074 | 3/1981 | Link . |
| 4,361,528 | 11/1982 | Ginsburg et al. . |
| 4,401,616 | 8/1983 | Wagner . |
| 4,403,961 | 9/1983 | Gurney . |
| 4,413,979 | 11/1983 | Ginsburg et al. . |
| 4,457,713 | 7/1984 | Schneider . |
| 4,569,342 | 2/1986 | von Nostitz . |
| 4,657,509 | 4/1987 | Morris . |
| 4,768,951 | 9/1988 | Abiru et al. . |
| 4,881,713 | 11/1989 | Wise . |
| 5,011,407 | 4/1991 | Pelerin . |
| 5,066,231 | 11/1991 | Oxman et al. . |
| 5,112,225 | 5/1992 | Diesso . |
| 5,135,392 | 8/1992 | Polansky . |
| 5,266,031 | 11/1993 | Marigza . |
| 5,267,862 | 12/1993 | Parker . |
| 5,336,086 | 8/1994 | Simmen et al. ............................ 433/37 |
| 5,415,544 | 5/1995 | Oxman et al. . |
| 5,431,563 | 7/1995 | Huybrechts . |
| 5,562,449 | 10/1996 | Jacobs et al. . |
| 5,591,786 | 1/1997 | Oxman et al. . |
| 5,753,781 | 5/1998 | Oxman et al. . |
| 5,961,325 | 10/1999 | Van Handel ............................. 433/37 |

METHOD AND APPARATUS FOR FABRICATING AND FITTING DENTURES

CROSS-REFERENCE TO RELATED APPLICATIONS

This application is a continuation of application Ser. No. 08/843,912 filed on Apr. 17, 1997, now U.S. Pat. No. 5,961,325.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

The present invention pertains generally to dentures, and more particularly to a simplified method and apparatus for fabricating and fitting dentures.

2. Description of the Background Art

Using conventional methods and devices for fabricating and fitting dentures, the dentist first takes an impression of the patient's dental arches. These impressions are then sent to the dental laboratory where the stone models of the patient's dental ridge are made.

At the laboratory, a dental technician then builds wax base plates on the stone dental ridges and mounts a wax biteblock on the base plates. These base plates are made by molding one or two layers of wax to conform to the stone model of the dental ridge. The biteblock is a spacer made of wax, shaped to conform to the curvature of the dental ridge, that establishes the space previously occupied by natural teeth.

The stone models and biteblocks are then returned to the dentist who registers the bite, which entails establishing the vertical, horizontal and depth plane of the upper dental ridge to the lower dental ridge by adjusting the upper and lower bite blocks accordingly. The dentist then selects a shade for the denture teeth and returns the biteblocks and stone models to the dental technician to be mounted on an articulator.

Back at the laboratory, the dental technician next selects the size of denture teeth according to the dimension of the dental stone models. Before the technician can start setting up the denture teeth, he must grind off the glaze of the truncated root portion of each denture tooth, so that there will be a bond between the teeth and the denture base material. After the teeth are set in position, wax is added to the base plate to form or simulate the gum tissue around each tooth. The dental setup is then returned to the dentist for a try-in in the patient's mouth.

The dentist then examines the dental setup in the patient's mouth. Once that procedure is complete, the dentist returns the setup to the laboratory technician for processing and polishing into a finished denture, and once again, it is sent back to the dentist for delivery to the patient. This multi-step process is time consuming and cumbersome, and requires several iterations between the dentist and the dental laboratory. Therefore, there is a need for a method and apparatus that will eliminate many of these steps, reduce the amount of time required for fabrication and fitting the dentures, and provide an easy and simple way for the dentist to complete the fabrication and fitting of dentures. The present invention satisfies those needs, as well as others, and overcomes the deficiencies inherent in conventional methods and devices for fabricating and fitting dentures.

BRIEF SUMMARY OF THE INVENTION

The foregoing needs are satisfied with a simplified method and apparatus for fabricating and fitting dentures in accordance with the present invention.

By way of example, and not of limitation, the present invention comprises plastic "Biteblock/Impression Trays" that are fabricated in large, medium and small sizes for both the upper and lower dental arches. Each tray has undercut grooves on the top and bottom surfaces to enhance adherence of a wax biteblock on one surface and use of impression material on the other surface. In addition, the lower trays are grooved at the midline to facilitate separation into two halves. The present invention further comprises "Preset Teeth Carrying Trays" that are fabricated in large, medium and small sizes corresponding to the sizes of the Biteblock/Impression Trays. The Preset Teeth Carrying Trays comprise artificial teeth, wax festooned around the teeth so as to resemble the gum tissue around natural teeth, and a plastic tray. Both the Preset Teeth Carrying Trays and the Biteblock/Impression Trays are fabricated in advance at a site of manufacture.

To prepare dentures, the dentist selects the appropriately sized lower and upper Biteblock/Impression Trays, takes lower and upper impressions of the patient's dental arches, adjusts the biteblocks for occlusal height, marks the midline, and attaches the upper and lower biteblocks to each other. The Biteblock/Impression Trays, which now include the impression of the dental ridges, are then sent to the dental laboratory with a color selection for the artificial teeth.

At the laboratory, the dental technician pours the impressions in stone without disturbing the attached biteblocks, mounts the stone models with attached biteblocks on an articulator, selects the correct size of teeth according to the shape of the dental arch, picks the shade of teeth the dentist specified and, with the biteblocks in place, sets the articulator to limit the extent of travel in the closed position of the lower jaw when the wax biteblocks are removed from the stone model. The technician then removes the Biteblock/Impression Trays, creates base plates for the upper and lower dental ridges. The technician removes the base plates for future use and resets the Biteblock/Impression Trays on the stone models.

Next, the lower biteblock on top of the Biteblock/Impression Tray and the rubber impression material are both cut at midline with a sharp knife. The plastic tray is then flexed so it breaks at the midline and either the right or left half of the tray is removed from the stone model of the dental ridge. One half of the base plate previously made is placed on the now exposed half of the stone model. Next, the wax on the lower Preset Teeth Carrying Tray is cut at the midline and the corresponding half is heated so that, from the midline on, these teeth can be slid off the tray, placed on the wax base plate, and adjusted to touch the upper biteblock and waxed into position. The remaining half of the lower Biteblock/Impression Tray is then removed from the dental ridge and the complementary half of the previously fabricated lower wax baseplate is placed on the stone dental ridge. The remaining and corresponding half of the Preset Teeth Carrying Tray is gently heated, the teeth setup is transferred to the wax base plate on the corresponding side of the stone model, and the wax-up procedure used on the previous half is duplicated. Next, the entire upper Biteblock/Impression Tray, as a unit, is removed. The upper wax base plate is fitted to the upper dental model, the underside of the entire upper Preset Teeth Carrying Tray is gently heated, and the upper setup of teeth is slid off the tray and waxed into position to occlude with the lower teeth.

The upper and lower stone models of the patient's dental ridges, along with the wax up of teeth, are then removed from the articulator and invested in stone in separate flasks. The stone investment in each flask is done as a two part process to accommodate separation of the two halves, upper and lower, at midline. After the stone has set up, the closed flasks are placed in boiling water to remove the wax that has been used to hold the teeth in the proper anatomical position. After this wax has been boiled away, each flask is opened at midline, and the boiling water is used to wash away all remaining traces of wax. The lower half of each set of flasks contains the dental ridges and the upper halves have the crowns of the teeth encased in stone. A separating medium is painted on the stone, and care should be taken not to get the separating medium on the roots of the teeth which would prevent the denture base, such as acrylic, from bonding to the roots of the teeth.

Currently known and used procedures are then followed to process the acrylic in boiling water, remove the processed denture with teeth attached, and polish. The denture is then ready for delivery to the dentist.

An object of the invention is to provide Biteblock/Impression Trays in which a dentist can directly take impressions of the patient's upper and lower arches instead of the dentist having to take impressions in impression trays and send the impression trays to a dental laboratory to have a technician pour them up in stone. This eliminates the need for the technician to build biteblocks on the stone models and return them to the dentist to register the bite, mark the midline and fasten the biteblocks together.

Another object of the invention is to provide Biteblock/Impression Trays with attached biteblocks that allow the dentist to register the bite, mark the midline and fasten the biteblocks together on the patient's first visit, thereby eliminating at least one visit.

Another object of the invention is to provide a disposable Biteblock/Impression Tray that will eliminate the need of sterilization for reuse as is now the practice.

Another object of the invention is to eliminate the need for the lab technician to craft biteblocks.

Another object of the invention is to dispense to the dental profession wax biteblocks and impression trays and the associated impression material as a single unit.

Another object of the invention is to provide a Preset Teeth Carrying Tray that increases the consistency of results by minimizing the individual handcrafting of each denture by different laboratory technicians.

Another object of the invention is to provide a Preset Teeth Carrying Tray that will eliminate the time consuming task of hand crafting the simulated gum tissue, grinding the glaze off of each individual tooth, and making a retention groove around each tooth.

Another object of the invention is to provide a Preset Teeth Carrying Tray wherein the teeth are preset in wax to simulate the supporting gum tissue and set on a plastic carrying tray.

Another object of the invention is to provide reusable molds for deglazing several sets of denture teeth and fabricating several sets of Preset Teeth Carrying Trays at the same time.

Another object of the invention is to eliminate the current unattractive method of delivering teeth to the lab technician on a flat block of plastic where the teeth are held in place by messy, sticky wax.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Figure 1:
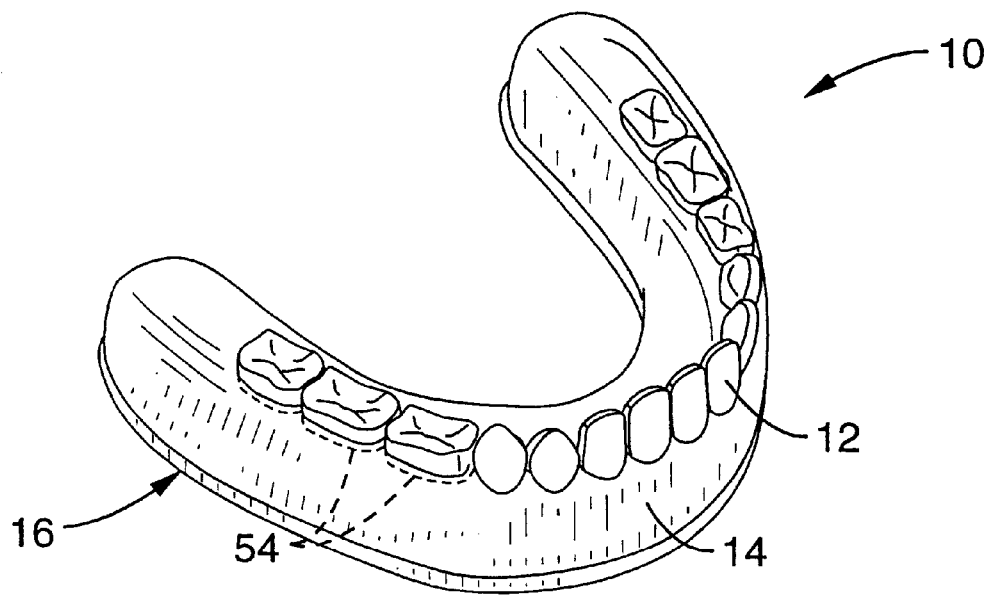
FIG. 1 is a top perspective view of a Preset Teeth Carrying Tray in accordance with the present invention.

Referring more specifically to the drawings, for illustrative purposes the present invention is embodied in the apparatus generally shown in FIG. 1 through FIG. 12 where like reference numerals denote like parts, and in the method described with reference thereto. It will be appreciated that the apparatus may vary as to configuration and as to details of the parts, and that the method of the invention may vary as to the steps and their sequence, without departing from the basic concepts as disclosed herein.

Figure 2:
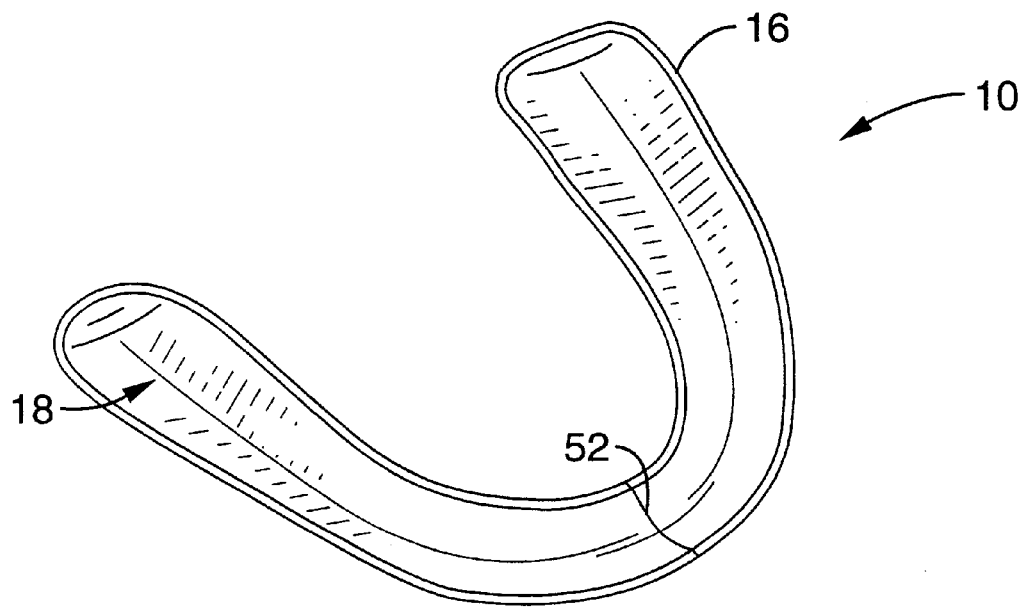
FIG. 2 is a bottom perspective view of the Preset Teeth Carrying Tray shown in FIG. 1.

Referring first to FIG. 1, a "Preset Teeth Carrying Tray" 10 in accordance with the present invention is shown for a lower denture. The Preset Teeth Carrying Tray 10 comprises a plurality of denture teeth 12 that are set in molded wax 14 that resembles the gum tissue surrounding natural teeth and that are supported by a support tray 16 made of plastic or like material. As can be seen in FIG. 1 and FIG. 2, the support tray 16 has a concave inner trough 18 and is generally shaped to conform to the shape of the dental arch. Note also that the wax 14 is festooned around the teeth 12 to resemble gum tissue found around natural teeth. For an upper denture, the Preset Teeth Carrying Tray 10 would be similar in configuration to the lower unit shown. Note that the denture teeth 12 will have the glaze removed from the roots and a retention groove 54 molded at the juncture of crown and root as described below. In addition, the teeth would be mounted in proper sequence according to size, mold and color, and Preset Teeth Carrying Trays can be made available in small, medium and large sizes to accommodate different sized dental arches.

Figure 3:
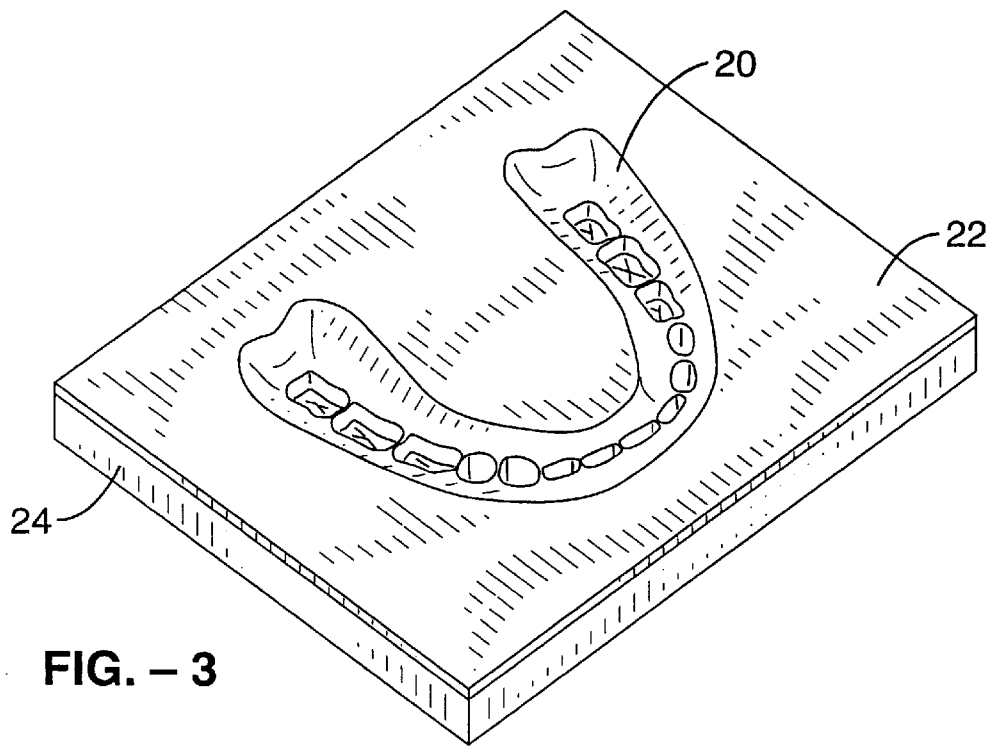
FIG. 3 is a perspective view of a mold for fabricating a Preset Teeth Carrying Tray in accordance with the present invention.
Figure 4:
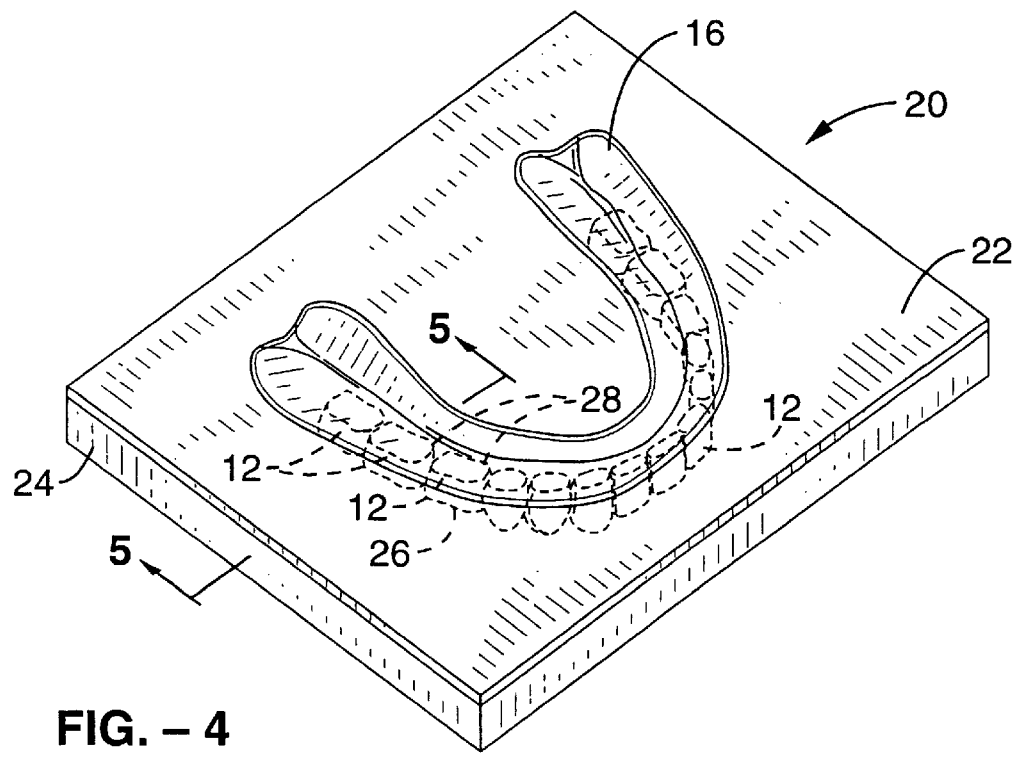
FIG. 4 is a perspective view of the mold of FIG. 3 showing the Preset Teeth Carrying Tray prior to removal.
Figure 5:
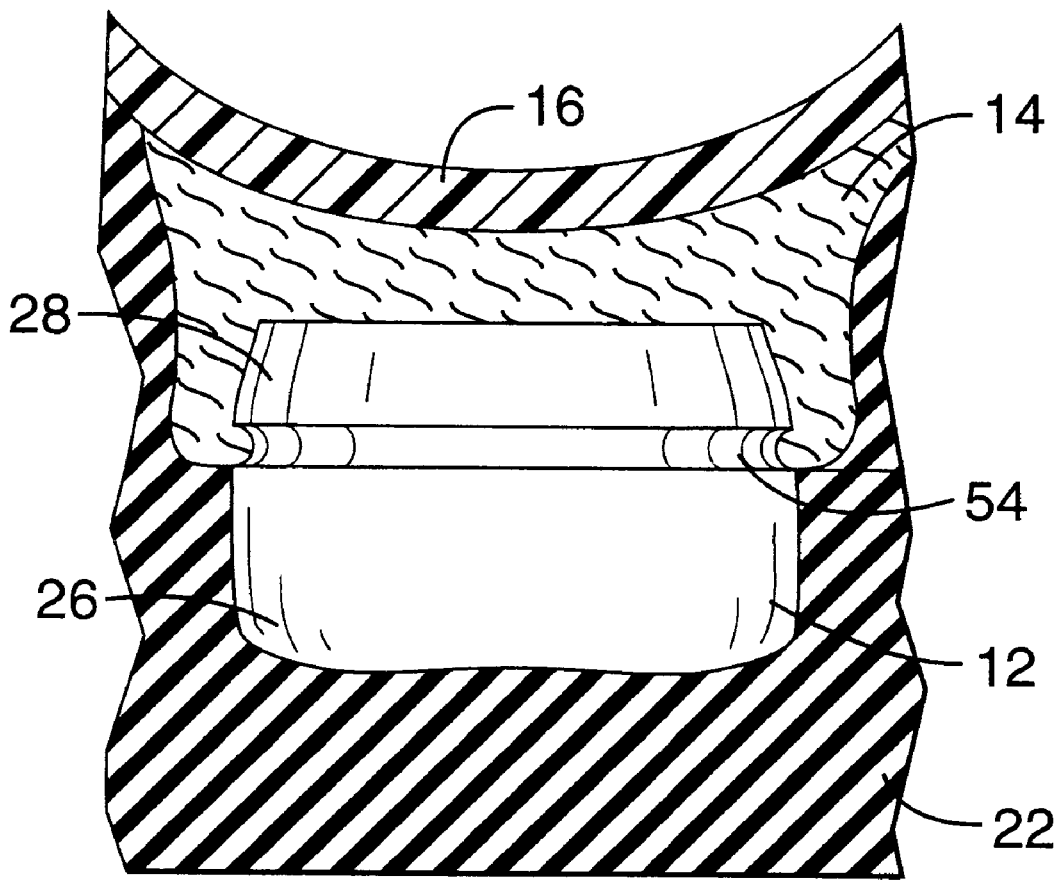
FIG. 5 is a fragmentary cross-sectional view of the assembly shown in FIG. 4 taken through line 5—5.
Figure 6:
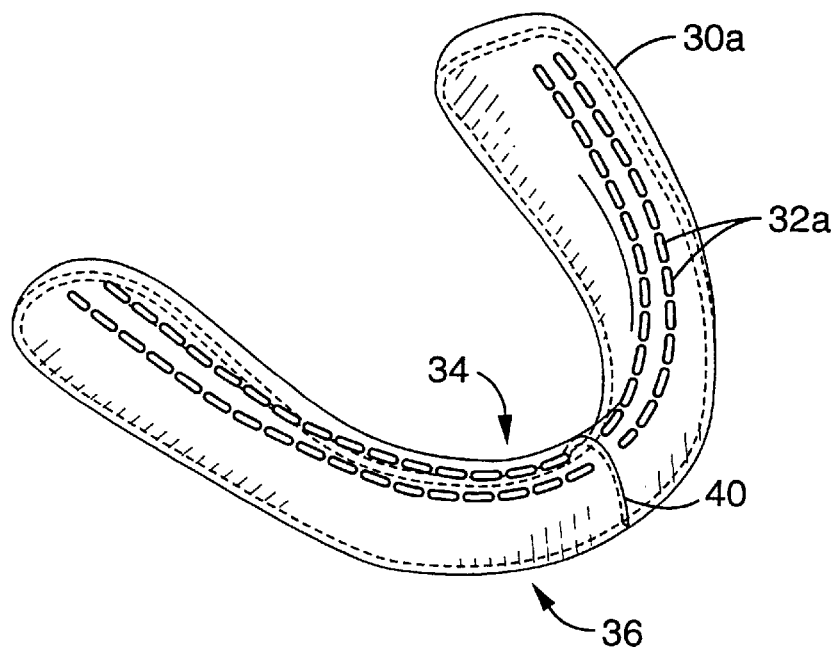
FIG. 6 is a top perspective view of a lower Biteblock/Impression Tray in accordance with the present invention, with the wax biteblock removed.
Figure 7:
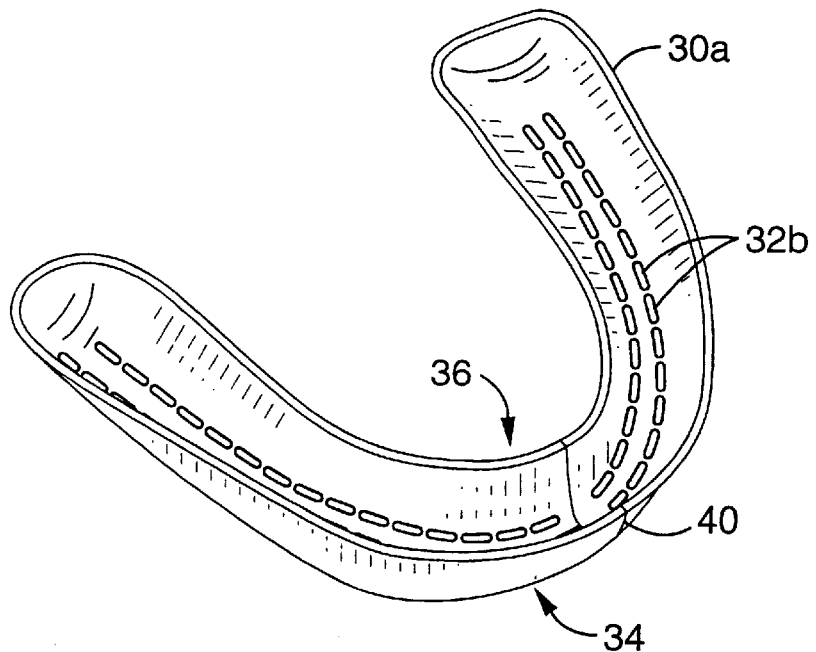
FIG. 7 is a bottom perspective view of the Biteblock/Impression Tray shown in FIG. 6.
Figure 8:
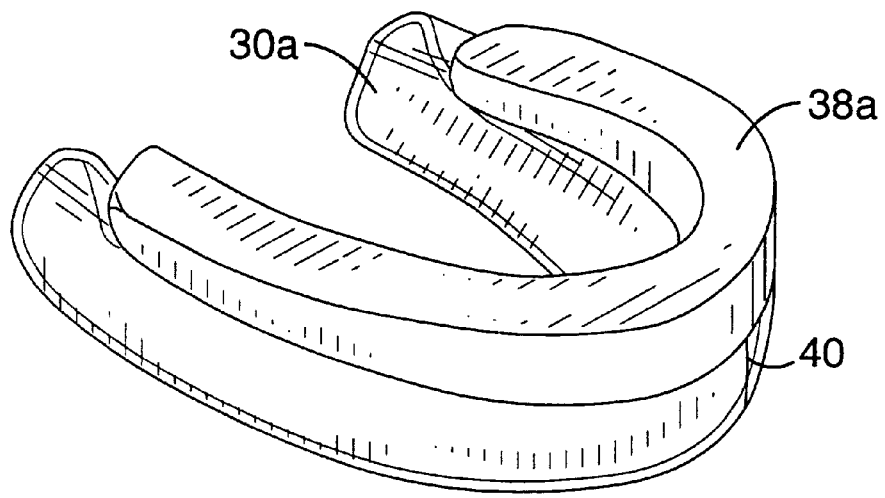
FIG. 8 is a top perspective view of the Biteblock/Impression Tray shown in FIG. 6 with a wax biteblock attached.
Figure 9:
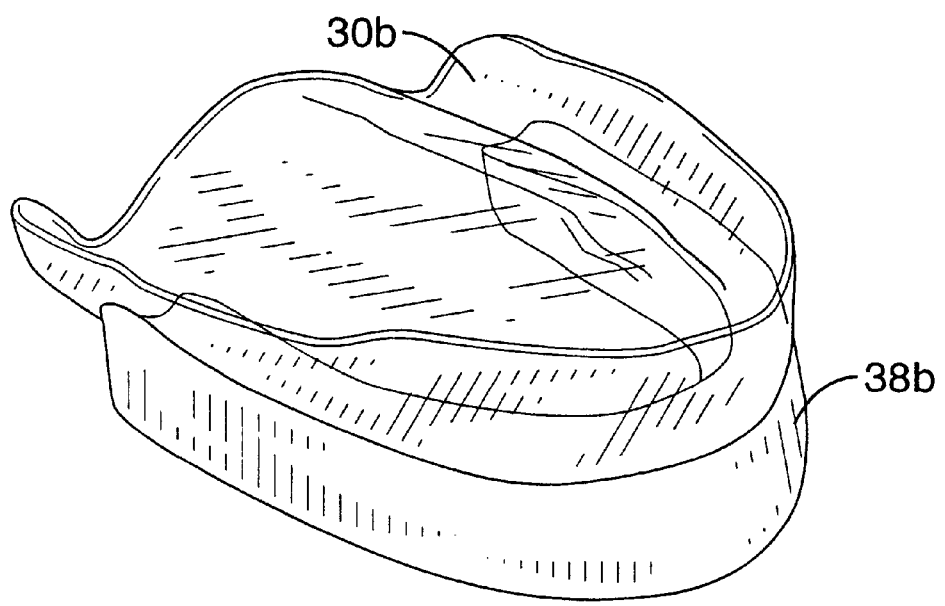
FIG. 9 is a top perspective view of an upper Biteblock/Impression Tray with a wax biteblock attached.

Referring also to FIG. 3 through FIG. 5, to fabricate a Preset Teeth Carrying Tray 10 a reusable rubber mold 20 of the negative impression of the anatomical arrangement of teeth and surrounding gum tissue is first made using reusable rubber impression material 22 which is held within a container 24. The denture teeth 12 with truncated roots are then mounted in the rubber impression material 22 with the denture teeth 12 placed in an inverted position such that the crowns 26 of the teeth are embedded in the rubber impression material 22 and the truncated roots 28 of the teeth are exposed. Note that denture teeth are typically manufactured with a glaze over the roots of the teeth. Therefore, a sand blaster or similar abrasive action must be used to remove the glaze from the roots of all of the teeth simultaneously. With the crowns of the teeth set in the rubber base impression material, the crowns will be protected from the abrasive action of sand or a like material when the roots are exposed to the blaster to remove the glaze.

Next, hot wax 14 is poured into the mold 20 around the truncated roots 28 of the denture teeth 12, and the plastic support tray 16 is pressed down until it contacts the truncated roots 28 of the denture teeth 12. The pouring of the hot wax 14 in mold 20 accomplishes the locking in place of the preset teeth 12 with the festooned wax margins of the gum tissue and, while the wax is still hot, the support tray 16 is set in place so that as soon as the wax is cooled the preset teeth and wax are attached to the support tray. When the wax has cooled, the Preset Teeth Carrying Tray 10 is removed from mold 20 as a single unit, without disturbing the setup or festooned wax around the roots of the teeth that resembles the gum tissue that would be around the natural teeth of the patient. In this regard, it is important to note that the teeth 12 and wax 14 retain their positions on the support tray 16. The rubber impression material 22 allows for the easy removal of the artificial denture teeth 12 after the wax 14 has flowed around the roots 28 and hardens. In this way, the mold 20 can be used again for production of additional units of the same size. Once fabricated, the Preset Teeth Carrying Trays are ultimately delivered to lab technicians for their inventory and use. Since the Preset Teeth Carrying Trays will have the denture teeth, with the glaze removed and a retention groove around each tooth, preset in position and the surrounding wax festooned to simulate the gum tissue, the dental technician will not have to remove the glaze, set up each tooth individually or carve and festoon the wax around each tooth. This will save the dental technician considerable time during the denture fabrication process.

Referring now to FIG. 6 through FIG. 9, lower 30a and upper 30b "Biteblock/Impression Trays" in accordance with the present invention are shown for the lower and upper arches, respectively. In practice, the Biteblock/Impression Trays would be fabricated in large, medium and small sizes for both the patient's upper and lower arches, with each tray having under-cut grooves 30a, 30b on the outer 34 and inner 36 surfaces to enhance adherence of a lower 38a or upper 38b wax biteblock on one side and future use of impression material (not shown) on the other side. Note that the top surface of the lower Biteblock/Impression Tray 30a is convex and carries the lower wax biteblock 38a and the bottom surface is concave to receive impression material. In addition, the lower trays have a groove 40 at their midline to facilitate the removal of half of the tray with the attached wax biteblock 38 to make room for the dental setup of teeth which will be transferred to a standard wax base plate 42 (FIG. 12) that will be set on a stone dental model. The lower Biteblock/Impression Tray 30a should be sufficiently deep for the dentist to take an impression of the patient's lower dental arch and shaped to conform to and simulate the shape of the dental arches. As can be seen from FIG. 9 which shows a Biteblock/Impression Tray 30b for an upper arch, the upper tray is configured to extend across the area between the dental ridges so as to accommodate the impression of the palate as well as the dental ridges.

To prepare dentures, the dentist must have impression material and a supply of lower 30a and upper 30b Biteblock/Impression Trays (e.g., small, medium and large) in his or her office. For a full set of dentures (upper and lower), the dentist would select the appropriate size of the Biteblock/Impression Trays to be used, and then take a lower and an upper impression of the patient's dental arches. Next, the dentist would reinsert the upper and lower Biteblock/Impression Trays into the mouth of the patient, adjust the biteblocks for occlusal height, mark the midline, and attach the upper and lower biteblocks to each other in a conventional manner. The dentist would then select the shade of the teeth desired for the denture. The Biteblock/Impression Trays, which now include the impression of the dental ridges, would then be sent to the dental laboratory with the color selection of the teeth. Note that the dentist saves considerable time since, with wax biteblocks attached, the dentist can take impressions of patients' dental ridges and register the occlusal height for the teeth, the midline, and the relationship of the upper and lower dental arches on the patient's first visit, before sending the Biteblock/Impression Trays to a laboratory technician.

At the laboratory the dental technician would then pour impressions in stone in a conventional manner using the Biteblock/Impression Trays without disturbing the attached biteblocks.

Next, the technician would select the correct Preset Teeth Carrying Trays 10 according to the size of the teeth, the shape of the dental arch, and the color of teeth the dentist specified.

Figure 10:
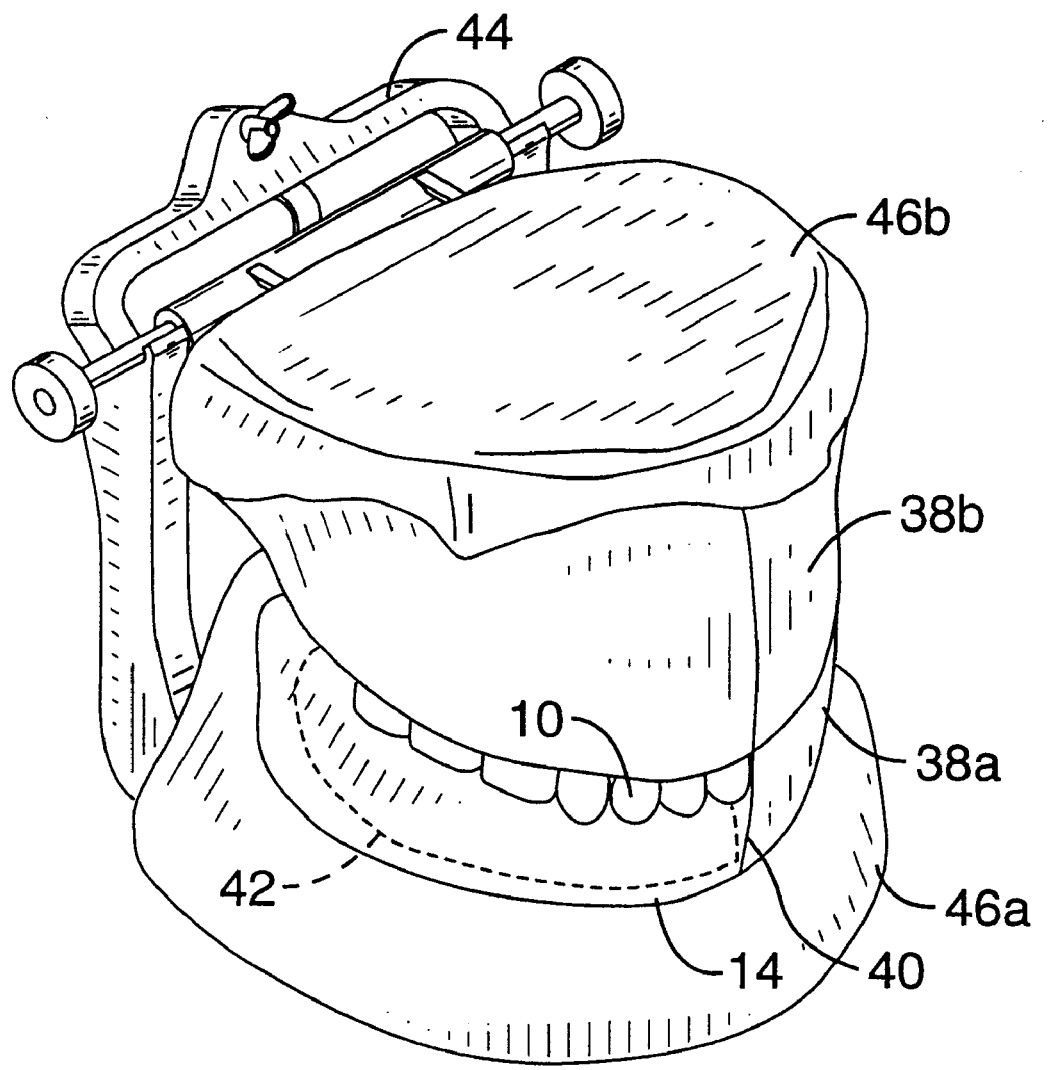
FIG. 10 is a perspective view showing upper and lower stone models mounted on an articulator, with the upper Biteblock/Impression Tray and upper wax biteblock in place, with one-half of the lower Biteblock/Impression Tray and lower wax biteblock in place, and with one-half of the lower set of denture teeth set in place of the other one-half of the lower Biteblock/Impression Tray and lower wax biteblock.
Figure 11:
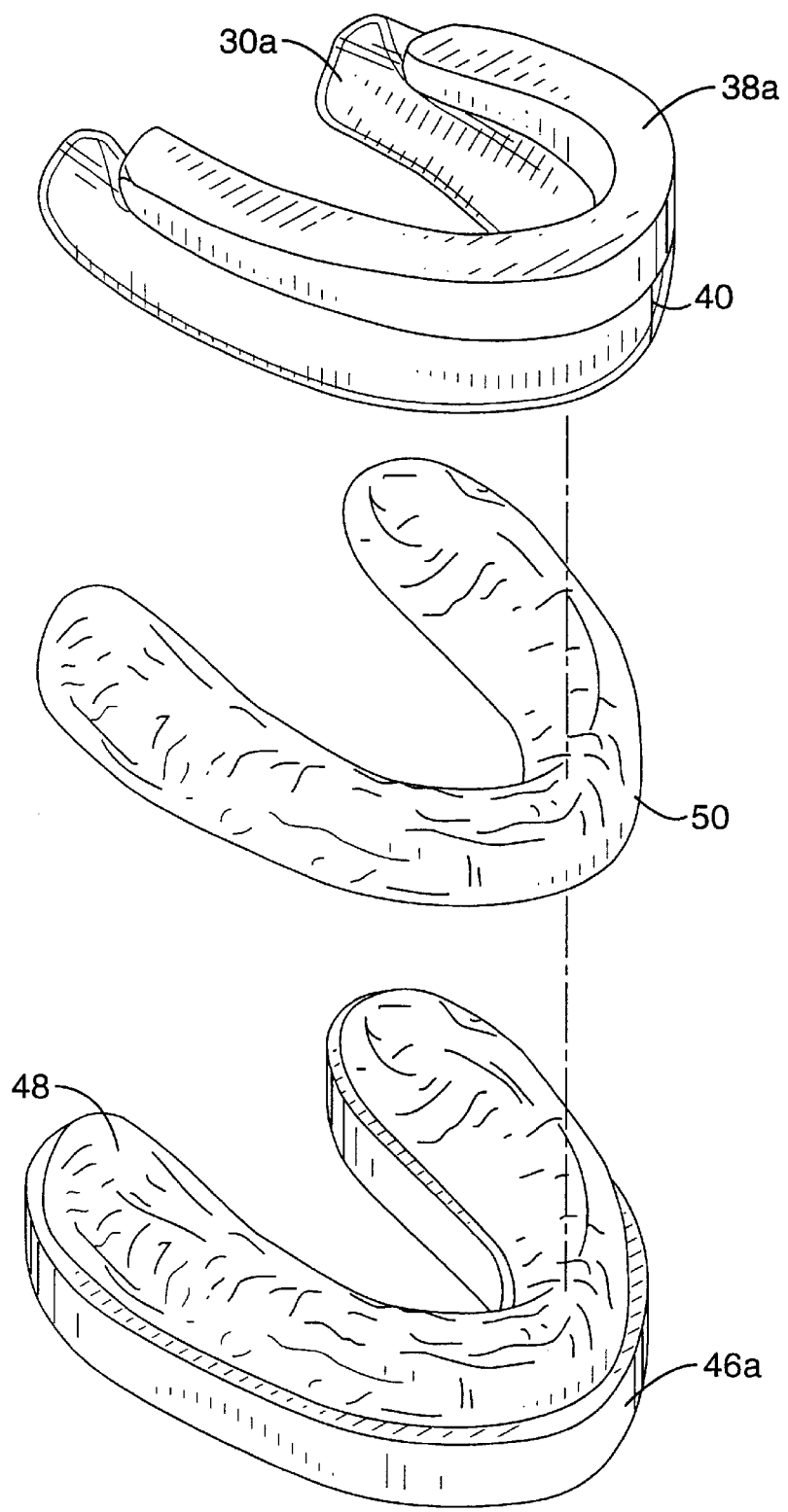
FIG. 11 is an exploded view of the lower Biteblock/Impression Tray, wax biteblock, and impression material portion of the assembly of FIG. 10 in relation to the lower stone model of the patient's dental arch prior to one-half of the lower set of denture teeth being set in place.
Figure 12:
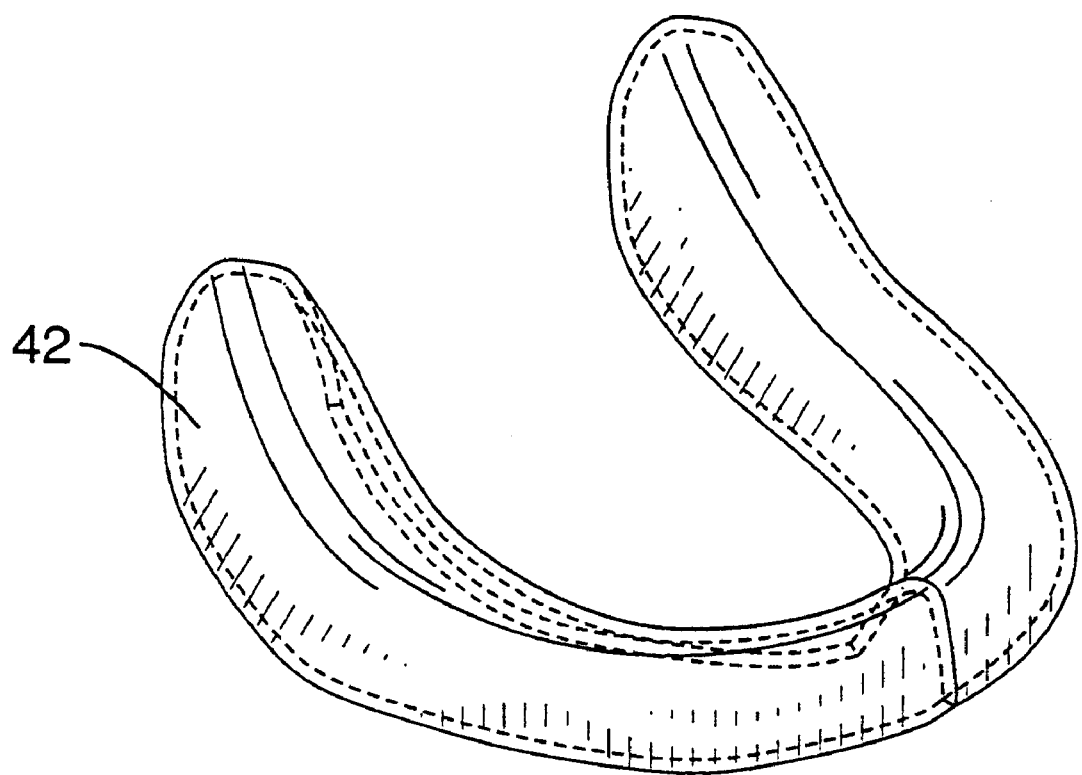
FIG. 12 is a top perspective view of a wax base plate employed in the present invention.

Referring also to FIG. 10 through FIG. 12, the dental technician mounts the Biteblock/Impression Trays and stone models on an articulator 44. With the biteblocks in place, the technician mechanically sets the articulator 44 to limit the extent of travel in the closed position of the lower jaw when the lower 38a and upper 38b wax biteblocks are removed from the lower 46a and upper 46b stone models. The technician then removes the upper and lower Biteblock/Impression Trays and creates base plates 42 for the upper and lower dental ridges 48. These base plates are then set aside temporarily. The Biteblock/Impression Trays are then reset on the stone models.

Next, the lower wax biteblock 38a on top of the lower Biteblock/Impression Tray 30a, and the rubber impression material 50 beneath the lower Biteblock/Impression Tray 30a are both cut at midline with a sharp knife. The plastic Biteblock/Impression Tray is then flexed so that it breaks at the midline with the assistance of the groove 40 (FIG. 6 and FIG. 7), and either the right or left half is removed from the stone model of the dental ridge. One half of the base plate 42 previously made is placed on the now exposed corresponding half of the stone model 46a. Next, the wax 14 on the lower Preset Teeth Carrying Tray 10 is cut at the midline and the corresponding half is heated from the underside of the support tray 16 so that, from the midline on, these teeth can be slid off the support tray 16, with the wax 14 and teeth 12 still intact, placed over the wax base plate 42, adjusted to occlude with the corresponding portion of the upper biteblock 38b, and waxed into position with care being taken not to disturb the wax 14 festooned around each tooth. The remaining half of the lower Biteblock/Impression Tray 30a is then removed from the dental ridge, and the teeth setup transferred to half of the wax base plate placed on that side of the stone model in the same manner. Again, care must be taken not to disturb the wax festooned around each tooth.

Thus far the procedure for transferring the lower denture teeth to the stone model has been described. To transfer the upper teeth to the stone model, the entire upper Biteblock/Impression Tray is removed as a unit. The upper wax base plate is then fitted to the upper stone model 46b. The underside of the entire upper Preset Teeth Carrying Tray is gently heated, and the upper setup of teeth is slid off the tray and waxed into position to occlude with the lower teeth, again using care so as not to disturb the anatomical wax setup around the teeth. Thus the entire wax setup and teeth can be transferred from the Preset Teeth Carrying Tray to the wax base plate on the upper stone model to match the occlusion of the opposing teeth. Note that the upper Biteblock/Impression Tray is not cut at the mid-line, as is done with the lower tray, but the entire upper Biteblock/Impression Tray is removed at one time, taking care that the articulator is locked in position; otherwise, the height for the upper teeth which had been established by the dentist with the biteblocks would be lost.

Once the wax-ups of the denture teeth on the stone models are complete as described above, the upper and lower stone models are then removed from the articulator, with the wax ups still intact, and invested in stone in separate casting flasks. The stone investment in each flask is done as a two part process, to accommodate separation of the two halves, upper and lower, at midline. After the stone has set up, the closed flasks are placed in boiling water to remove the wax that has been used to hold the teeth in the proper anatomical position. After this wax has been boiled away, each flask is opened at midline, and the boiling water is used to wash away all remaining traces of wax. At this point, the lower half of each set of flasks will contains the dental ridges and the upper halves will have the crowns of the teeth encased in stone. A separating medium is then painted on the stone, with care being taken to ensure that the separating medium does not contact the roots of the teeth since it would prevent the denture base, such as acrylic, from bonding to the roots of the teeth. The denture base is then applied in a conventional manner, and standards procedures followed to process the acrylic in boiling water, remove the processed denture with teeth attached, and polish the denture. The denture is then ready for delivery to the dentist.

Referring again to FIG. 2, note that support tray 16 includes a midline notch 52 to facilitate separating the support tray into two halves during fabrication. In addition, note from FIG. 1 and FIG. 5 that the denture teeth 12 are manufactured with a retention groove 54 around the tooth at the junction between the crown 26 and the root 28.

From the description above, those skilled in the art will appreciate that the present invention provides a number of advantageous features that include, but are not limited to:

1. The Biteblock/Impression Trays can be made from disposable plastic trays with wax biteblocks attached, in which the dentist can take impressions.
2. Removal of the glaze on the truncated root portion of the denture teeth on the Preset Teeth Carrying Trays can be completed before leaving the dental manufacturing facility.
3. Removal of the glaze on the roots of all preset teeth on a Preset Teeth Carrying Tray can be effected simultaneously in a matter of seconds.
4. A retention groove can be molded at the juncture of the root and crown of each tooth while at the manufacturing facility. This retention groove will provide a mechanical lock to insure imbedment of the tooth in the denture base material.
5. The Preset Teeth Carrying Trays will have the denture teeth preset in wax according to mold and shade before leaving the manufacturing facility.
6. The Preset Teeth Carrying Trays will have the denture teeth preset on a disposable plastic carrying tray, which will be done at the manufacturing facility.
7. The wax containing the denture teeth on the Preset Teeth Carrying Tray can be removed easily from the disposable carrying tray.
8. On the Preset Teeth Carrying Trays, the wax containing the lower denture teeth is molded to not only hold the denture teeth in place, but is festooned to simulate the labial, buccal and lingual surfaces of the lower denture.
9. On the Preset Teeth Carrying Trays, the wax containing the upper denture teeth is molded not only to hold the denture teeth in place, but festooned to simulate the labial and buccal surfaces of the upper denture.
10. The Preset Teeth Carrying Tray has the denture teeth previously set up by the dental manufacturer to be delivered to the dental technician, thereby eliminating the need for the dental technician to set the teeth individually.
11. The Preset Teeth Carrying Tray is a convenient way to allow the wax and denture teeth to be shipped without distortion.
12. Delivering the teeth on the Preset Teeth Carrying Tray with the glaze removed saves the dental laboratory technician much valuable time by not having to grind the glaze off each individual tooth.
13. The preset teeth carrying tray has the teeth preset in a dental arch instead of on a flat surface where each tooth has to be set up individually, thus saving the dental laboratory technician much time.
14. The teeth set up on the Preset Teeth Carrying Tray, with wax simulating the surrounding gum tissue, is more presentable than teeth set on a flat surface.
15. The Biteblock/Impression Tray, with wax biteblocks, can be mounted on an articulator, and the teeth from the Preset Teeth Carrying Tray can be transferred to a wax base plate by removing one half of the lower Biteblock/Impression Tray at the midline, gently heating the underside of the corresponding side of the Preset Teeth Carrying Tray, and sliding the teeth onto the base plate.
16. By having the teeth touch the upper biteblock, the occlusal height of the lower teeth can be established.

17. By carefully adding wax to the wax base plate and the block of preset teeth, the teeth can be set in position on the stone models without disturbing the pre-contoured wax around the teeth.
18. The articulator can be set so that the height will not be changed when the entire upper Biteblock/Impression Tray is removed from the upper stone model.
19. The entire upper Biteblock/Impression Tray, including the plastic base plate and impression material, can be removed from the upper stone model and a wax base plate adapted to the stone model.
20. The entire bottom of the upper Preset Teeth Carrying Tray can be gently heated so that the complete upper preset teeth can be slid off the Preset Teeth Carrying Tray and waxed into position on the upper wax base plate.
21. Having the teeth preset on the Preset Teeth Carrying Tray will save the laboratory technician much setup time.
22. The Preset Teeth Carrying Tray, with the wax surrounding the teeth already anatomically formed, will save the dental laboratory technician a significant amount of bench time.
23. Both the lower Biteblock/Impression Tray and the lower Preset Teeth Carrying Tray are notched at the midline so that when the wax is cut, the trays can be separated easily at the midline.
24. Both the upper and lower impression trays have flanges to facilitate the taking of impressions.
25. The upper Biteblock/Impression Tray has a palate to facilitate taking an impression of the upper dental ridge and palate.
26. The upper Preset Teeth Carrying Tray can be made without a palate so that the tray cannot be improperly used to take an impression.
27. Both the upper and lower Preset Teeth Carrying Trays can be made without flanges to preclude the use of these trays for taking impressions.
28. The plastic tray used in the Biteblock/Impression Tray has undercuts on both the upper and lower sides to enhance adherence of the wax biteblock on one side and the adherence of the impression material on the other side.
29. Use of the Biteblock/Impression Tray will reduce the number of appointments for the patient.
30. Use of the Biteblock/Impression Tray allows the dentist, on the patient's first visit, to take impressions, register the patient's bite, establish the height for the upper and lower denture teeth by the height of the biteblocks, establish the midline of upper and lower, and seal the upper and lower biteblocks to establish the patient's position of the upper and lower dental arches to each other.
31. If only a single denture is to be made, a single Biteblock/Impression Tray can be used, in which case the same procedures can be used as with both dentures except that it will not be necessary to seal the upper and lower biteblocks. Instead, to establish the position of the upper and lower arches to each other, the opposing arch with natural teeth bites into the soft wax of the biteblock on the Biteblock/Impression Tray. The dentist takes an impression of the natural teeth. Then a stone model is made from the impression and this stone model will occlude with the teeth marks in the Biteblock/Impression Tray.

Accordingly, it will be seen that this invention provides a simplified apparatus and method for fabrication and fitting dentures compared to conventional devices and methods. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. An apparatus for fabricating dentures, comprising:
   (a) a biteblock/impression tray, said biteblock/impression tray having a convex outer surface and a concave inner surface;
   (b) a wax biteblock attached to said outer surface of said biteblock/impression tray;
   (c) said concave inner surface of said biteblock/impression tray configured for receiving impression material; and
   (d) a plurality of surface deformations along said outer surface of said biteblock/impression tray, said surface deformations disposed between said outer surface of said biteblock/impression tray and said wax biteblock.

2. An apparatus as recited in claim 1, further comprising a plurality of surface deformations along said inner surface of said biteblock/impression tray.

3. An apparatus as recited in claim 1, wherein said biteblock/impression tray includes first and second ends, and wherein said biteblock/impression tray further includes a groove in its outer surface positioned midline between said first and second ends.

4. An apparatus for fabricating dentures, comprising:
   (a) a biteblock/impression tray, said biteblock/impression tray having a convex outer surface and a concave inner surface;
   (b) a wax biteblock attached to said outer surface of said biteblock/impression tray;
   (c) said concave inner surface of said biteblock/impression tray configured for receiving impression material; and
   (d) a plurality of depressions along said outer surface of said biteblock/impression tray, said depressions disposed between said outer surface of said biteblock/impression tray and said wax biteblock.

5. An apparatus as recited in claim 4, further comprising a plurality of surface deformations along said inner surface of said biteblock/impression tray.

6. An apparatus as recited in claim 4, wherein said biteblock/impression tray includes first and second ends, and wherein said biteblock/impression tray further includes a groove in its outer surface positioned midline between said first and second ends.

* * * * *

UNITED STATES PATENT AND TRADEMARK OFFICE
CERTIFICATE OF CORRECTION

PATENT NO. : 6,149,427
DATED : November 21, 2000
INVENTOR(S) : William J. Van Handel It is certified that error appears in the above-identified patent and that said Letters Patent is hereby corrected as shown below:

Column 7,
Line 53, change "contains" to -- contain --

Signed and Sealed this

Nineteenth Day of July, 2005

JON W. DUDAS
*Director of the United States Patent and Trademark Office*